United States Patent
Watanabe

(10) Patent No.: US 10,483,144 B2
(45) Date of Patent: Nov. 19, 2019

(54) METHOD FOR DETERMINING FRONT AND BACK OF SINGLE-CRYSTAL WAFER

(71) Applicant: SHIN-ETSU HANDOTAI CO., LTD., Tokyo (JP)

(72) Inventor: Shiroyasu Watanabe, Jyoetsu (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 119 days.

(21) Appl. No.: 15/754,410

(22) PCT Filed: Aug. 18, 2016

(86) PCT No.: PCT/JP2016/003773
§ 371 (c)(1),
(2) Date: Feb. 22, 2018

(87) PCT Pub. No.: WO2017/038034
PCT Pub. Date: Mar. 9, 2017

(65) Prior Publication Data
US 2018/0247851 A1 Aug. 30, 2018

(30) Foreign Application Priority Data
Sep. 3, 2015 (JP) ................................. 2015-174024

(51) Int. Cl.
*G01N 23/20* (2018.01)
*H01L 21/68* (2006.01)
(Continued)

(52) U.S. Cl.
CPC ........... *H01L 21/68* (2013.01); *G01N 23/207* (2013.01); *G01N 23/20008* (2013.01); *G01N 2223/6116* (2013.01)

(58) Field of Classification Search
CPC . H01L 21/68; G01N 23/20008; G01N 23/207
See application file for complete search history.

(56) References Cited

U.S. PATENT DOCUMENTS 4,995,063 A 2/1991 Enoki et al.
5,073,918 A * 12/1991 Kamon ................ G01N 23/207
378/205
(Continued)

FOREIGN PATENT DOCUMENTS

JP H02-190751 A 7/1990
JP H02-218945 A 8/1990

OTHER PUBLICATIONS

Nov. 1, 2016 International Search Report issued in International Patent Application No. PCT/JP2016/003773.

*Primary Examiner* — Kiho Kim
(74) *Attorney, Agent, or Firm* — Oliff PLC

(57) ABSTRACT

A method for determining front and back of a single-crystal wafer including: using, as the single-crystal wafer, one having a crystal plane which is laterally asymmetrical to a reference direction connecting a center of a cut for orientation identification formed in an end face of the single-crystal wafer with a center of the single-crystal wafer; noticing the laterally asymmetrical crystal plane, applying an X-ray to the single-crystal wafer, and detecting a diffracted X-ray to measure an angle formed between an orientation of the noticed crystal plane and the reference direction; and determining whether a surface of the single-crystal wafer is a front surface or a back surface from a value of the measured angle. Consequently, the method for determining a front and a back of a single-crystal wafer which can assuredly determine the front and the back of the single-crystal wafer and is superior in cost can be provided.

12 Claims, 3 Drawing Sheets

(51) Int. Cl.
   *G01N 23/207*  (2018.01)
   *G01N 23/20008*  (2018.01)

(56) References Cited

U.S. PATENT DOCUMENTS

| | | | | |
|---|---|---|---|---|
| 8,462,913 B2 * | 6/2013 | Evans | ............... | G21K 1/025 |
| | | | | 378/147 |
| 9,678,023 B2 * | 6/2017 | Kim | ............... | G01N 23/207 |
| 2003/0128809 A1 * | 7/2003 | Umezawa | ............ | G01N 23/20 |
| | | | | 378/70 |

* cited by examiner (a)    (b)

METHOD FOR DETERMINING FRONT AND BACK OF SINGLE-CRYSTAL WAFER

TECHNICAL FIELD

The present invention relates to a method for determining a front and a back of a single-crystal wafer.

BACKGROUND ART

Silicon single crystal wafers are widely used for manufacture of semiconductor devices. As the silicon single crystal wafers, wafers whose front surface is a (100) crystal plane are often used. As to such a silicon single crystal wafer, since a front side of a wafer has a cleaving direction or characteristics at the time of manufacturing a semiconductor device which are equal to counterparts of a back side of the same, even if the front side and the back side of the wafer are countercharged in a process of manufacturing silicon single crystal wafers from a single-crystal ingot of silicon, no problem arises. (However, the above may not be applicable when different treatments have been applied to the front side and the back side of the wafer, respectively).

On the other hand, Patent Literature 1 discloses a need for making a determination on wafer front and back sides of each silicon single crystal wafer sliced off with an off-angle so that slicing is performed from a specific lattice plane at a slant at the time of slicing a single-crystal ingot.

Further, to determine a front side and a back side of the silicon single-crystal wafer, there is also disclosed a method for determining the front and back by applying an X-ray from an X-ray source having a relative position fixed to the silicon single crystal wafer, detecting a diffracted X-ray from a crystal plane with an off-angle by a detector having a relative position fixed to the silicon single crystal wafer, and comparing an output from the detector with a predetermined threshold value.

CITATION LIST

Patent Literature

Patent Literature 1: Japanese Unexamined Patent Publication (Kokai) No. Hei 02-218945

DISCLOSURE OF INVENTION

Problem to be Solved by the Invention

However, the method for determining a front and a back disclosed in Patent Literature 1 does not deal with determination of a front and a back of a single-crystal wafer having no off-angle.

Further, as a method for determining a front and a back of a single-crystal wafer without a need for a complicated apparatus, there is a method for determining in which direction (an angle) a cleavage plane is present relative to a reference direction connecting a center of a notch (or an orientation flat) formed in the single-crystal wafer with a wafer center by actually cracking the single-crystal wafer. However, since this front and back determining method based on the cleavage is a destructive inspection, an inspected wafer is discarded and disadvantageous in terms of cost, and the inspection is a so-called sampling test and does not 100% guarantee the front and the back of the wafer which turns to a product.

In view of the problem, it is an object of the present invention to provide a method for determining a front and a back of a single-crystal wafer, which assuredly determines a front and a back of a single-crystal wafer and is superior in costs.

Means for Solving Problem

To achieve the object, the present invention provides a method for determining a front and a back of a single-crystal wafer comprising:

using, as the single-crystal wafer, one having a crystal plane which is laterally asymmetrical to a reference direction connecting a center of a cut for orientation identification formed in an end face of the single-crystal wafer with a center of the single-crystal wafer;

noticing the laterally asymmetrical crystal plane, applying an X-ray to the single-crystal wafer, and detecting a diffracted X-ray to measure an angle formed between an orientation of the noticed crystal plane and the reference direction; and determining whether a surface of the single-crystal wafer is a front surface or a back surface from a value of the measured angle.

In this manner, measuring the angle formed between the orientation of the noticed crystal plane and the reference direction by the X-ray diffraction enables assuredly determining the front and the back in a non-destructive manner. Thus, the front and the back can be determined at a low cost, and the front and the back of each single-crystal wafer can be 100% guaranteed when a total inspection is performed.

At this time, it is possible that an orientation deviation of the cut from a predetermined orientation is measured by obtaining a difference between an actual measured value and a theoretical value of the angle formed between the orientation of the noticed crystal plane and the reference direction as well as performing the determination of a front and a back.

In this manner, obtaining the difference between the actual measured value and the theoretical value of the angle formed between the orientation of the noticed crystal plane and the reference direction enables measuring the orientation deviation of the cut from the predetermined orientation without separately performing additional measurement.

At this time, it is possible that, as the single-crystal wafer which is subjected to the determination of a front and a back, a wafer whose wafer main surface has a crystal plane {1 1 0} is used.

When such a single-crystal wafer is used, the method for determining a front and a back of a single-crystal wafer according to the present invention can be preferably applied. It is to be noted that, here, {1 1 0} represents a plane group equivalent to (1 1 0).

At this time, it is preferable that, when the wafer whose wafer main surface has the crystal plane {1 1 0} is used as the single-crystal wafer which is subjected to the determination of a front and a back, the orientation of the noticed crystal plane is an orientation of a (1 −1 0) plane.

When attention is focused on such a crystal plane, the present invention can be particularly preferably applied. It is to be noted that, in notation of each crystal plane, to express a minus numerical figure, a bar should be superscribed above it, but the minus numerical figure is written as it is for the convenience of notation (in the following description, minus numerical figures may be written as they are in some situations).

At this time, it is preferable that the cut for orientation identification is a notch or an orientation flat.

In this manner, if the cut for orientation identification is the notch or the orientation flat, it is widely generally used, and hence any special treatment does not have to be performed to each single crystal wafer.

Effect of the Invention

As described above, according to the present invention, since a front and a back of a single-crystal wafer having a crystal plane which is laterally asymmetrical to a reference direction connecting a center of a cut formed in an end face of the wafer with a center of the wafer can be assuredly determined in a non-destructive manner, the low-cost front and back determination can be carried out, and the front and the back of each single-crystal wafer can be 100% guaranteed by performing a total inspection. Furthermore, the front and the back can be determined, and an orientation deviation of the cut from a predetermined orientation can be also measured.

BEST MODE(S) FOR CARRYING OUT THE INVENTION

The present invention will now be described hereinafter in more detail.

As described above, in the method for determining a front and a back of a single-crystal wafer, the method for determining a front and a back of a sing-crystal wafer by which the front and the back are assuredly determined in a non-destructive manner is demanded.

As a result of conducting the earnest examination to achieve the object, the present inventor has found out that the problem can be solved by the method for determining a front and a back of a single-crystal wafer including:

using, as the single-crystal wafer, one having a crystal plane which is laterally asymmetrical to a reference direction connecting a center of a cut for orientation identification formed in an end face of the single-crystal wafer with a center of the single-crystal wafer;

noticing the laterally asymmetrical crystal plane, applying an X-ray to the single-crystal wafer, and detecting a diffracted X-ray to measure an angle formed between an orientation of the noticed crystal plane and the reference direction; and determining whether a surface of the single-crystal wafer is a front surface or a back surface from a value of the measured angle, thereby bringing the present invention to completion.

An embodiment of the present invention will now be described hereinafter in detail with reference to the drawings, but the present invention is not restricted thereto.

With miniaturization of semiconductor devices, requests for silicon single crystal wafers have recently become rigorous and diversified. In such requests, there is a request to determine a tail portion side (a crucible side) of a single-crystal ingot pulled by a CZ (Czochralski) method as a front surface side (a mirror-polished surface side) of each wafer. This will now be described with reference to FIG. 2.

Figure 2:
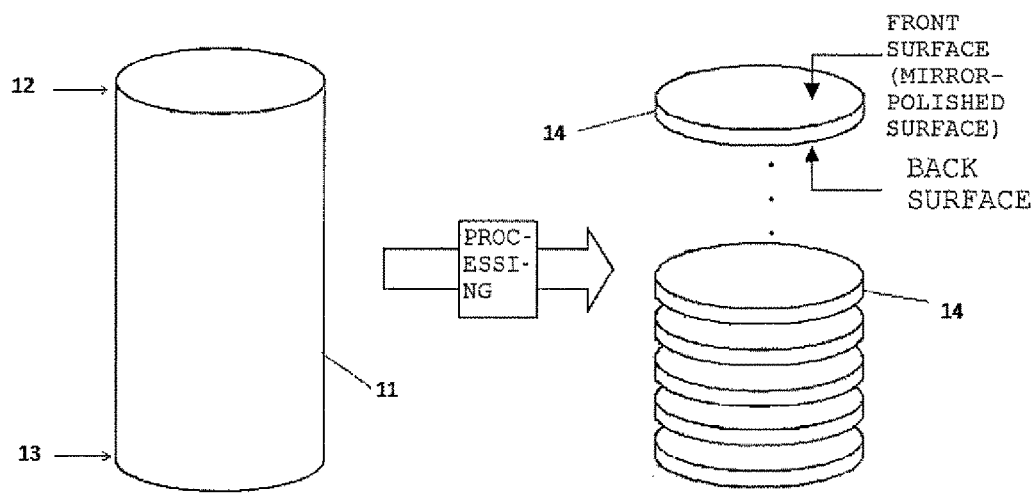
FIG. 2 is a schematic view showing that a single-crystal ingot is processed into product wafers.

FIG. 2 is a schematic view showing that a single-crystal ingot is processed into product wafers. A single-crystal silicon ingot 11 in FIG. 2 is arranged in such a manner that its upper side becomes a tail portion side 12 and its lower side becomes a seed side 13. The single-crystal silicon ingot 11 is processed into product silicon single crystal wafers 14 through later-described slicing, chamfering, and measurement of an orientation deviation of a cut, polishing, various inspection processes, and the like. In conventional examples, to assuredly guarantee that a front surface of each product wafer is the tail portion side 12 of the single-crystal silicon ingot 11, close attention must be paid so that a front and a back are not changed (are maintained) in a series of processing and inspection processes, and a wafer must be sampled in an important process to confirm the front and the back by a destructive inspection configured to confirm a cleavage. However, even if the product silicon single-crystal wafers 14 are manufactured in this manner, the inspection is the destructive inspection, the front and the back of each product silicon single crystal wafer 14 cannot be guaranteed 100%.

Moreover, as a cut formed in an end face of each single-crystal wafer for orientation identification, a notch or an orientation flat is generally used, but there is also a request to put an orientation deviation of this cut from a predetermined orientation within a very strict standard. For example, on a desired value level, there is a request to put a deviation amount from a predetermined orientation within ±10' (minutes). Thus, the orientation deviation of the cut must be easily measured with a high accuracy in accordance with each single-crystal wafer.

Here, an apparatus which can be used in the method for determining a single-crystal wafer according to the present invention will now be described. The apparatus used in the method for determining a front and a back of a single-crystal wafer according to the present invention includes an X-ray source which irradiates each wafer with X-rays, an X-ray detector which detects a diffracted X-ray from a crystal plane of each wafer, and a sample holding mechanism which holds each single-crystal wafer. At this time, the diffracted X-ray is detected in a direction along which an incoming X-ray and a crystal plane of each wafer meets the Bragg's law. Thus, it is preferable for the sample holding mechanism to include a mechanism which rotates each wafer, and for the X-ray detector to include a moving mechanism. As the apparatus having such a structure, there is a diffractometer.

Figure 1:
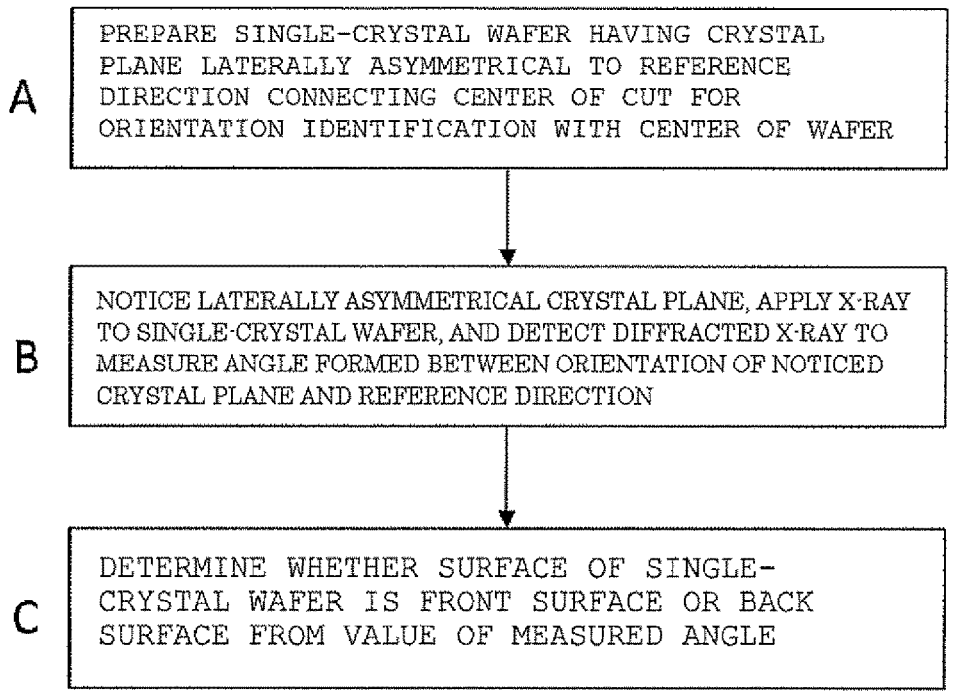
FIG. 1 is a view showing a process flow of a method for determining a front and a back of a single-crystal wafer according to the present invention.

Next, the method for determining a front and a back of a single-crystal wafer according to the present invention will be described with reference to FIG. 1. FIG. 1 is a view showing a process flow of the method for determining a front and a back of a single-crystal wafer according to the present invention. In the method for determining a front and a back of a single-crystal wafer according to the present invention, as indicated by a process A in FIG. 1, as a single-crystal wafer which is an inspection target, a single-crystal wafer having a crystal plane laterally asymmetrical to a reference direction connecting a center of a cut for orientation identification with a center of the wafer is prepared.

Figure 3:
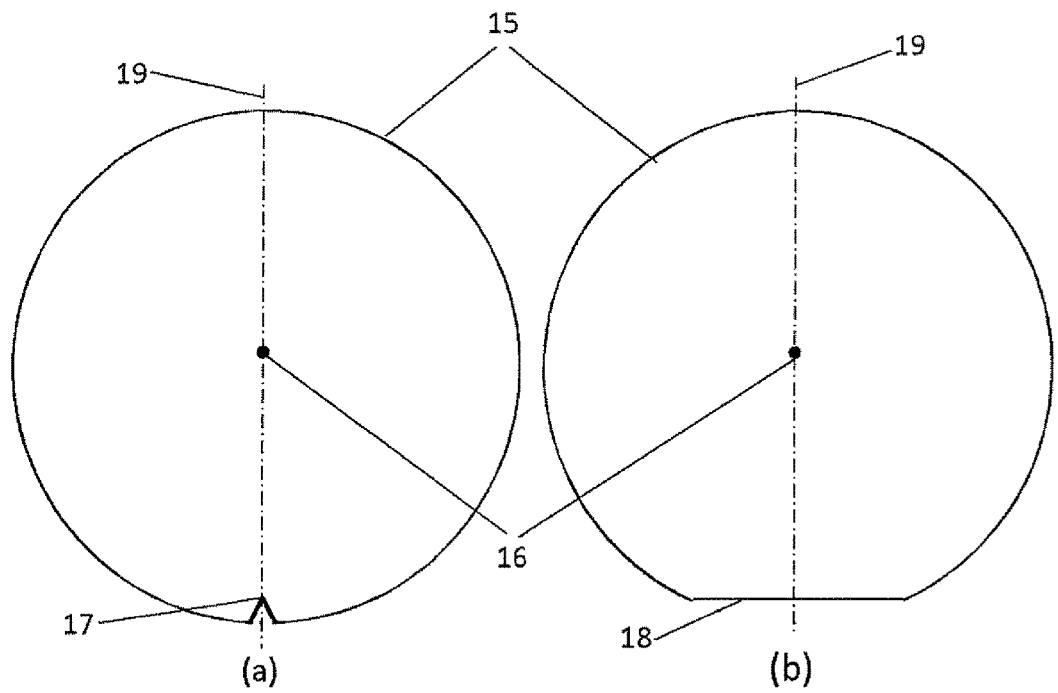
FIG. 3 is a schematic view showing a cut ((a) a notch, (b) an orientation flat)

As the cut of orientation identification, there is a notch or an orientation flat as described above. Here, the center of the cut is a point which correctly indicates an orientation specified by the notch or the orientation flat and, for example, when the cut is a notch 17 shown in FIG. 3(a), a top of the notch can be the center of the cut. Additionally, when the cut is an orientation flat 18 as shown in FIG. 3(b), for example, a middle point of the orientation flat can be the center of the cut. Further, a direction indicated by a straight line connecting the center of the notch 17 with a center 16 of a wafer 15 becomes a reference direction 19. Likewise, a direction indicated by a straight line connecting the middle point of the orientation flat 18 with the center 16 of the wafer becomes the reference direction 19.

Figure 4:
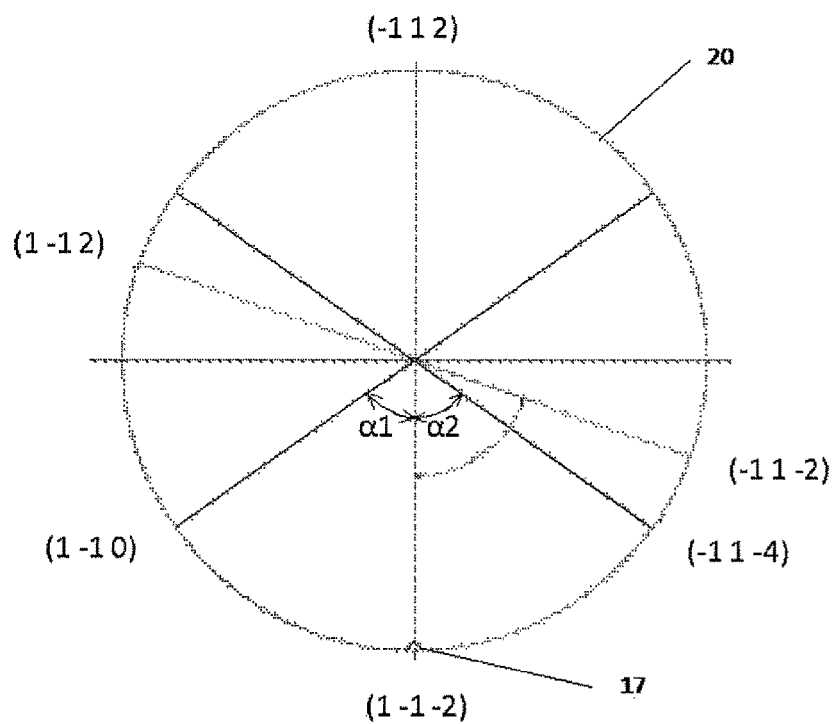
FIG. 4 is a schematic view showing an orientation of a crystal plane of a silicon single crystal wafer which can be used in the method for determining a front and a back of a single-crystal wafer according to the present invention.

Here, a single-crystal wafer having a crystal plane asymmetrical to the reference direction will be further described with reference to FIG. 4. FIG. 4 is a schematic view showing an example of an asymmetric crystal plane and orientations of cleavage when the silicon single crystal wafer is seen from a seed side. A main surface shown in FIG. 4 is a {1 1 0} plane, and FIG. 4 shows the silicon single crystal wafer 20 with a notch 17 having an orientation of a (1 −1 −2) plane.

In FIG. 4, for example, a (1 −1 0) plane is a laterally asymmetric crystal plane and can be a noticed crystal plane. Further, a crystal plane laterally symmetrical to the (1 −1 0) plane is a (−1 1 −4) plane, and an orientation of the original (1 −1 0) plane becomes an orientation of the (−1 1 −4) plane when the wafer is reversed. Assuming that an angle formed between the orientation of the (1 −1 0) plane and the reference direction is $\alpha_1$ and an angle formed between the orientation of the (−1 1 −4) plane and the reference direction is $\alpha_2$, an absolute value of $\alpha_1$ is equal to that of $\alpha_2$. Assuming that a clockwise direction is positive (plus), $\alpha_1$=−54.74°. Furthermore, the orientation of the (1 −1 −2) and the orientation of the (1 −1 2) plane are directions of cleavage.

As described above, in the wafer whose wafer main surface has the crystal plane {1 1 0}, since the crystal plane which is laterally asymmetrical to the reference direction is included, the present invention can be preferably applied.

Moreover, when a single-crystal wafer whose wafer main surface has the crystal plane {1 1 0} is used as a single-crystal wafer which is subjected to the front and back determination, an orientation of a noticed crystal plane can be an orientation of a (1 −1 0) plane. In such a single-crystal wafer, the noticed crystal plane has the orientation shown in FIG. 4, and the present invention can be preferably applied.

Next, the laterally asymmetric crystal plane of the prepared single crystal wafer is noticed, an X-ray is applied to the single-crystal wafer, and a diffracted X-ray is detected to measure an angle formed between an orientation of the noticed crystal plane and the reference direction (a process B in FIG. 1). As already described with reference to FIG. 4, when the single-crystal wafer is reversed, the noticed crystal plane does not appear at its original position. In this case, even if the X-ray is applied to the position in which the noticed crystal plane in the single-crystal wafer should be included, the diffracted X-ray which meets the predetermined Bragg's law is not detected. Thus, when a relative positional relationship of the single-crystal wafer and the incoming X-ray is adjusted and the diffracted X-ray is detected, the angle formed between the orientation of the noticed crystal plane and the reference direction can be measured. An actual measured value of the angle formed between the orientation of the noticed crystal plane and the reference direction may be referred to as $\beta$ in the following description.

Subsequently, whether the surface of the single-crystal plane is a front surface or a back surface is determined from a value of the measured angle (a process C in FIG. 1). The orientation of the noticed crystal plane varies depending on the front surface, the back surface, or an end face from which the single-crystal wafer is seen, and the angle formed between each of these orientations and the reference angle also varies as a matter of course. A theoretical value of each of these angles can be obtained by a calculation in advance (the theoretical value of the angle may be referred to as a hereinafter). Thus, comparing the angle $\beta$ actually measured in the process B with the theoretical angle $\alpha$ enables determining the front and the back of the single-crystal wafer.

Further, when a difference ($\beta-\alpha$) between the actual measured value $\beta$ and the theoretical value $\alpha$ of the angle formed between the orientation of the noticed crystal plane and the reference direction is obtained in addition to execution of the determination of the front and the back, an orientation deviation of the cut from a predetermined orientation can be measured. When an appropriate X-ray diffractometer is used, the angle formed between the orientation of the noticed crystal plane and the reference direction can be accurately obtained. Thus, the orientation deviation of the cut can be obtained from a value of ($\beta-\alpha$). Here, the predetermined orientation means an orientation of a crystal plane indicating an orientation of the cut.

Although the method for determining a front and a back of a single-crystal wafer according to the present invention has been described above, an effect of applying the method for determining a front and a back of a single-crystal wafer according to the present invention to a step of processing a single-crystal ingot into product single crystal wafers will now be described hereinafter with reference to FIG. 5.

Figure 5:
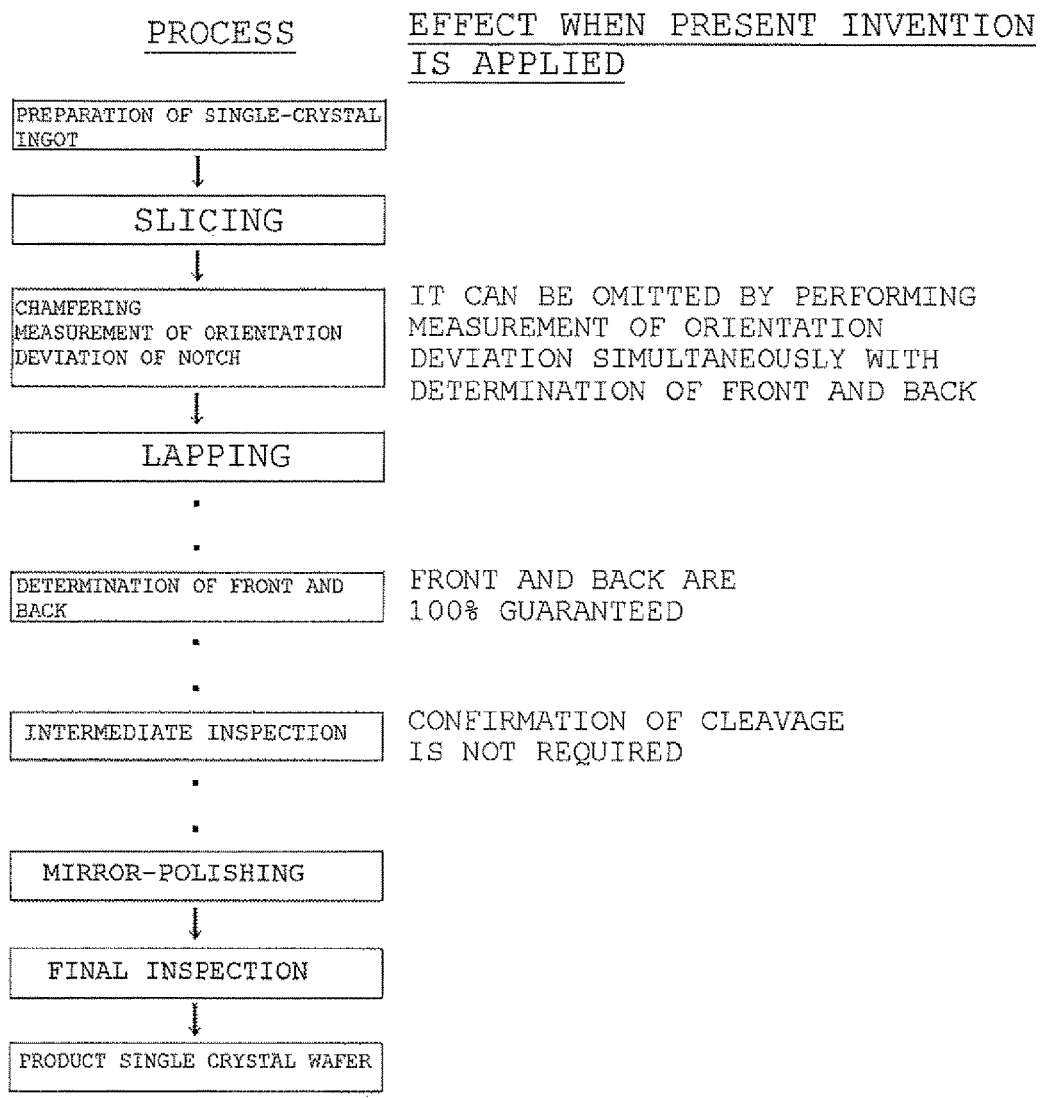
FIG. 5 is a view showing a process flow of processing a single-crystal ingot into a product single crystal wafer.

FIG. 5 is a view showing a process flow of processing the single-crystal ingot into the product single crystal wafers. Processes which do not directly relate to the description of the present invention are appropriately omitted.

The single-crystal ingot having a cut formed therein is processed into a wafer shape by slicing.

Furthermore, execution of the determination of a front and a back of a single-crystal wafer according to the present invention is provided either before or after subsequent processes such as chamfering and lapping. It is to be noted that, in the chamfering, an orientation deviation of a notch is measured. A position of the front and back determination shown in FIG. 5 is an illustrative example, and it is not restricted to this position. In this example, it is preferable to perform the determination of a front and a back of a single-crystal wafer according to the present invention immediately before a process of making a front and a back visually distinguishable, e.g., irregular shape chamfering (chamfering with a chamfering width which differs depending front and back sides), laser marking, external gettering, or polishing, or after such a process. When the determination of a front and a back is performed immediately before the process of making the front and the back of each single-crystal wafer visually distinguishable, the front or the back is not processed by mistake, and hence disposal of the single-crystal wafers due to wrong processing can be eliminated. Moreover, when the determination of a front and a back is performed after the process of making the front and the back of each single-crystal wafer visually distinguishable, it is possible to confirm whether the process has been correctly performed. Additionally, the number of times of carrying out the present invention in the process flow from the single-crystal ingot to the product crystal wafers is not restricted in particular. Further, the number of wafers which are subjected to the front and back determination per lot is not restricted in particular, but a total inspection is preferable to guarantee 100%.

In conventional examples, one to several wafers are subjected to the front and back determination based on cleavage per lot in a subsequent intermediate inspection process, but such a destructive inspection does not have to be carried out in the process flow, shown in FIG. 5, to which the present invention is applied. Thus, the wafer disposal in the intermediate inspection process can be eliminated.

Further, the front surface side of each single-crystal wafer is mirror-polished, and it turns to a product single-crystal wafer through a polished wafer inspection (PW inspection) process.

EXAMPLES

Although the present invention will now be more specifically described hereinafter with reference to examples, the present invention is not restricted thereto.

Example 1

20 silicon single crystal wafers each having a laterally asymmetric crystal plane based on a specification (a product name A) shown in the following Table 1 were prepared. Cuts of these wafers are all notches. It is to be noted that the product name A has a noticed crystal plane (1 −1 0) at a position shown in FIG. 4. Furthermore, in this example, attention was focused on a laterally asymmetrical crystal plane which appears in an end face of each wafer.

TABLE 1

| Product name | Specification | Orientation of notch | Noticed crystal plane | α (°) | Crystal plane when reversed |
|---|---|---|---|---|---|
| A | Diameter: 200 mm Crystal plane of main surface: {1 1 0} | (1 −1 −2) | (1 −1 0) | 54.74 | (−1 1 −4) |

Each of the 20 silicon single crystal wafers having the product name A were subjected to a front and back determining inspection based on the method for determining a front and a back of a single-crystal wafer according to the present invention for 10 times so that the inspection was carried out for 200 times in total. The front and the back were reversed for a predetermined number of times in the 200 times of the inspection, and whether the front and the back were able to be correctly determined was evaluated. Table 2 shows results.

TABLE 2

| Product name | Normal/reversal setting | | | Determination result | | | Erroneous determination rate |
|---|---|---|---|---|---|---|---|
| | Normal | Reversal | Total | Normal | Reversal | Total | |
| A | 189 | 11 | 200 | 189 | 11 | 200 | 0% |

As shown in Table 2, an erroneous determination was not made at all on the silicon single crystal wafer of each product name. In this manner, according to the method for determining a front and a back of a single-crystal wafer of the present invention, the front and the back of each silicon single crystal wafer was able to be determined with an accuracy of 100%.

Example 2

Three silicon single crystal wafers having a product name A were prepared. Each silicon single crystal wafer was inspected by the method for determining a front and a back according to the present invention for 10 times to measure an orientation deviation of each notch. Table 3 shows results.

TABLE 3

| | | Wafer No. | | |
|---|---|---|---|---|
| Type | Item | 1 | 2 | 3 |
| A | Reference value | +1' 00" | +0' 40" | +1' 00" |
| | Measurement result 1 | +1' 29" | +1' 30" | +1' 28" |
| | 2 | +1' 37" | +1' 38" | +1' 32" |
| | 3 | +1' 30" | +1' 48" | +1' 44" |
| | 4 | +1' 42" | +1' 55" | +1' 51" |
| | 5 | +1' 31" | +1' 49" | +1' 41" |
| | 6 | +1' 38" | +1' 43" | +1' 50" |
| | 7 | +1' 50" | +2' 02" | +1' 37" |
| | 8 | +1' 47" | +1' 48" | +1' 44" |
| | 9 | +1' 48" | +1' 56" | +1' 43" |
| | 10 | +1' 52" | +1' 50" | +1' 56" |
| | Ave | +1' 40" | +1' 48" | +1' 43" |
| | Reference value difference | +0' 40" | +1' 08" | +0' 43" |
| | Standard deviation | 8.7" | 9.2" | 8.6" |

In Table 3, the reference value is a value measured by a conventional apparatus. The reference value difference is a difference between an average value of 10 measurements of the orientation deviation of the notch and the reference value. The standard deviation is a standard deviation obtained from 10 measured values of the orientation deviation of the notch of each wafer. An absolute value of the reference value difference of each wafer having the product name A was within 1 minute and 10 seconds, and the standard deviation of the same was within 10 seconds. It has been revealed from this result that the orientation deviation of the cut from a predetermined orientation can be obtained with a high accuracy by the method for determining a front and a back of a single-crystal wafer according to the present invention. Moreover, in this system, performing the measurement of the orientation deviation of the notch as well as the front and back determination enables omitting an independent process of measuring the orientation deviation of the notch in a chamfering process.

It is to be noted that the present invention is not restricted to the embodiment. The embodiment is an illustrative example, and any example which has substantially the same structure and exerts the same functions and effects as the technical concept described in claims of the present invention is included in the technical scope of the present invention.

The invention claimed is:

1. A method for determining a front and a back of a single-crystal wafer comprising:
   using, as the single-crystal wafer, one having a crystal plane which is laterally asymmetrical to a reference direction connecting a center of a cut for orientation identification formed in an end face of the single-crystal wafer with a center of the single-crystal wafer;
   noticing the laterally asymmetrical crystal plane, applying an X-ray to the single-crystal wafer, and detecting a diffracted X-ray to measure an angle formed between an orientation of the noticed crystal plane and the reference direction; and
   determining whether a surface of the single-crystal wafer is a front surface or a back surface from a value of the measured angle.

2. The method for determining a front and a back of a single-crystal wafer according to claim 1, wherein an orientation deviation of the cut from a predetermined orientation is measured by obtaining a difference between an actual measured value and a theoretical value of the angle formed between the orientation of the noticed crystal plane and the reference direction as well as performing the determination of a front and a back.

3. The method for determining a front and a back of a single-crystal wafer according to claim 2, wherein, as the single-crystal wafer which is subjected to the determination of a front and a back, a wafer whose wafer main surface has a crystal plane {1 1 0} is used.

4. The method for determining a front and a back of a single-crystal wafer according to claim 3, wherein, when the wafer whose wafer main surface has the crystal plane {1 1 0} is used as the single-crystal wafer which is subjected to the determination of a front and a back, the orientation of the noticed crystal plane is an orientation of a (1 −1 0) plane.

5. The method for determining a front and a back of a single-crystal wafer according to claim 4, wherein the cut for orientation identification is a notch or an orientation flat.

6. The method for determining a front and a back of a single-crystal wafer according to claim 3, wherein the cut for orientation identification is a notch or an orientation flat.

7. The method for determining a front and a back of a single-crystal wafer according to claim 1, wherein, as the single-crystal wafer which is subjected to the determination of a front and a back, a wafer whose wafer main surface has a crystal plane {1 1 0} is used.

8. The method for determining a front and a back of a single-crystal wafer according to claim 7, wherein, when the wafer whose wafer main surface has the crystal plane {1 1 0} is used as the single-crystal wafer which is subjected to the determination of a front and a back, the orientation of the noticed crystal plane is an orientation of a (1 −1 0) plane.

9. The method for determining a front and a back of a single-crystal wafer according to claim 8, wherein the cut for orientation identification is a notch or an orientation flat.

10. The method for determining a front and a back of a single-crystal wafer according to claim 7, wherein the cut for orientation identification is a notch or an orientation flat.

11. The method for determining a front and a back of a single-crystal wafer according to claim 1, wherein the cut for orientation identification is a notch or an orientation flat.

12. The method for determining a front and a back of a single-crystal wafer according to claim 2, wherein the cut for orientation identification is a notch or an orientation flat.

* * * * *